(12) United States Patent
Roques et al.

(10) Patent No.: US 6,391,866 B1
(45) Date of Patent: May 21, 2002

(54) (α-AMINOPHOSPHINO) PEPTIDES DERIVATIVE AND COMPOSITIONS CONTAINING SAME

(75) Inventors: Bernard Roques; Marie-Claude Fournie-Zaluski, both of Paris; Xuixiong Chen, Bagneux, all of (FR)

(73) Assignee: Institut National de la Sante et de la Recherche Medicale (Inserm), Paris Cedex (FR)

( * ) Notice: Subject to any disclaimer, the term of this patent is extended or adjusted under 35 U.S.C. 154(b) by 0 days.

(21) Appl. No.: 09/673,842
(22) PCT Filed: Apr. 20, 1999
(86) PCT No.: PCT/FR99/00921
§ 371 Date: Feb. 9, 2001
§ 102(e) Date: Feb. 9, 2001
(87) PCT Pub. No.: WO99/54336
PCT Pub. Date: Oct. 28, 1999

(30) Foreign Application Priority Data

Apr. 22, 1998 (FR) .............................. 98 05009

(51) Int. Cl.[7] .......................... C07F 9/32; A61K 31/662
(52) U.S. Cl. ....................................... 514/119; 558/170
(58) Field of Search ................... 558/170, 178, 558/179, 207; 514/119

(56) References Cited

FOREIGN PATENT DOCUMENTS

| EP | 0 053 902 | 6/1982 |
| WO | WO 95/35302 | 12/1995 |
| WO | WO 96/33201 | 10/1996 |
| WO | WO 97/00261 | 1/1997 |
| WO | WO 98/18803 | 5/1998 |

OTHER PUBLICATIONS

By S. Chackalamannil et al., "Highly Potent and Selective Inhibitors of Endothelin Converting Enzyme", Bioorganic & Medicinal Chemistry Letters, vol. 6, No. 11, 1996, pp. 1257–1260.

By H. Chen et al., "Aminophosphinic inhibitors as transition state analogues of enkephalin–degrading enzymes: A class of central analgesics", Proceesings of The National Academy of Sciences of USA, vol. 95, No. 20, Sep. 1998, pp. 12028–12033.

*Primary Examiner*—Robert W. Ramsuer
*Assistant Examiner*—Kamal Saeed
(74) *Attorney, Agent, or Firm*—Young & Thompson

(57) ABSTRACT

The invention concerns (α-aminophosphino) peptide derivative compounds of general formula (I) wherein: $R_1$ and $R_2$ represent each a hydrogen atom or together form an imine with the adjacent nitrogen atom; $R_3$ represents an alkyl group, an alkenyl group, a phenyl group, a benzyl group, all said groups capable of being substituted or not, a hydrogen atom, a cycloalkyl group, a cycloalkylmethyl group or finally a methyl group substituted by an aromatic or saturated heterocyclic group; $R_4$ represents a CH(X)—(O)—C(O)—Y group or a $CH_2CH_2$—S—C(O)—W group; $R_5$ represents an alkyl group, an alkenyl group, a phenyl group, a benzyl group, all said groups capable of being substituted or not, a hydrogen atom, a cycloalkyl group, a cycloalkylmethyl group or finally a methyl group substituted by an aromatic or unsaturated heterocyclic group; $R_6$ and $R_7$ can in particular represent a hydrogen atom, an alkyl group, a phenyl group substituted or not; $R_8$ represents an alkyl, alkenyl, phenyl or benzyl group; n=0 or 1, in the form of enantiomers, diastereoisomers or racemic mixtures, their salts, the method for preparing them and their therapeutic applications.

(I)

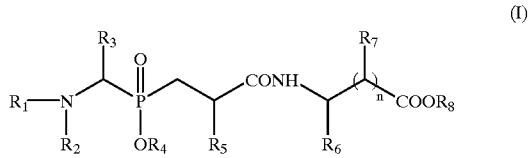

5 Claims, No Drawings

(α-AMINOPHOSPHINO) PEPTIDES DERIVATIVE AND COMPOSITIONS CONTAINING SAME

This application is a 371 of PCT/FR99/00921, filed Apr. 20, 1999.

The perception, transmission and regulation of the nociceptive influxes are dependent on several endogenous neuraltransmitters. In 1975, Hugues et al. (*Nature*, 258, 577, 1975) have identified enkephalines, two primitively isolated pentapeptides of mammal brains which are implicated in the transmission of painful influx. Enkephalines connect with at least two classes of receptors: the opioid sites a and 6 (Pert, *Sciences*, 179, 1011, 1973) whose roles and locations are different. Their antinociceptive properties have been demonstrated by Belluzi et al., *Nature*, 260, 625, 1976. However, the analgesia induced by administration of exogenous enkephalines is very fleeting, because of the rapid metabolism of these peptides. Analogous enkephalines rendered resistant to enzymatic degradation by chemical modifications, have been synthesized, but their secondary effects are analogous to those of morphine.

The enkephalines are physiologically degraded by two types of enzymatic activity which metabolize in vivo the enkephalines: neutral endopeptidase (EC 3.4.24.11, also called NEP) which cuts the $Gly^3Phe^4$ bond and aminopeptidase N (EC 5 3.4.11.2, also called APN) which cuts the $Tyr^1$-$Gly^2$ bond (reviewed in Roques et al., *Pharmacol. Rev.*, 45, 87–146, 1993).

There are known prodrugs described in European patent EP 0 487 620 and in Fournié-Zaluski et al., *J. Med. Chem.*, 35, 2473, 1992, which have analgesic and antidepressive activities after intravenous administration or by oral route (Noble et al., *J. Pharm. Exp. Ther.*, 261, 181, 1992; Baamonde et al., *Eur. J. Pharmacol.*, 216, 157, 1992). However, these compounds do not respond to the concept of mixed inhibitors, because of their structure in which an APN inhibitor and an NEP inhibitor are is associated with a disulfide bridge. These compounds are then reduced by cerebral reductases and each act on its particular target.

According to the patent application WO 95/35302 and *Bioorganic and Medicinal Chemistry Letters*, Vol. 6, No. 11, pp. 1257–1260, 1996, there are known certain derivatives of phosphenic acid having respectively an inhibiting activity on the enzyme conversion of endotheline (ECE) and a mixed inhibitory activity of the enzyme of conversion of angiotensin (ACE) and of neutral endopeptidase (NEP). These compounds are useful in the treatment of cardiovascular maladies.

Derivatives of α-aminophosphino peptides are described in the patent application PCT/FR9701884.

One of the objects of the invention is to provide new compounds, which behave as true mixed inhibitors of APN and NEP, capable of conjointly inhibiting the two enzymatic activities responsible for the degradation of the enkephalines and to manifest their pharmacological properties after intravenous or subcutaneous injection, or by oral route (per os).

These compounds have certain properties of the morphine substances, in particular analgesia, the beneficial effects on the behavior (antidepressants, sedatives, anxiolytics, desinhibitors and promnesics), and peripheral effects (antidiuretic, antitussive, hypotensive, anti-inflammatory . . .). Moreover, an advantage of these compounds is that they have no undesirable morphine effects (tolerance, physical and psychic dependence, respiratory depression, intestinal statis . . .).

The compounds can also be used as a treatment for substitution in the toxiconomy of opioides.

The present invention has for its object compounds derived from α-aminophosphino peptides of the general formula

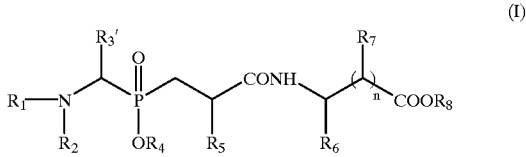

in which $R_1$ and $R_2$ each represent a hydrogen atom or $R_1$ and $R_2$, taken together, form an unsaturated group of the formula R' (R")C=, in which R' represents a phenyl group in position 2 monosubstituted with a hydroxy group or a disubstituted phenyl group, in position 2, with a hydroxy group and, in position 4 or 5, either by a halogen atom or by a nitro group, or by a hydroxy group, or by an alcoxy group —$OR_9$, R" represents a phenyl group, a phenyl group substituted with 1 to 5 halogen atoms or an aromatic heterocyclic group, in what follows, the terms $R_9$ and $R_{10}$, used for the definition of the radicals, each represent an alkyl group of 1 to 6 carbon atoms, $R_3$ represents a hydrogen atom, an alkyl group or an alkenyl group of 1 to 6 carbon atoms, these two latter groups can be substituted by:

a hydroxy group or an alcoxy group —$OR_9$, a phenyl group or a benzyl group, a sulfanyl group, an alkylsulfanyl group —$SR_9$ or an alkylsulfanyl group oxidized at the sulfur atom —$S(O)R_9$, an amino group, an —$NHR_9$ group or —$NR_9R_{10}$ group, if desired oxidized at the nitrogen atom or, a guanidino group $H_2N$—C(=NH) —NH—, a cycloalkyl or cycloalkylmethyl group, a phenyl group, a benzyl group, which can be substituted on the phenyl group with 1 or 2 of the following substituents:

a halogen atom, a hydroxy group, an alcoxy group —$OR_9$, an alkylsulfanyl group —$SR_9$ or an alkylsulfanyl group oxidized at the sulfur atom, an amino group or a —$NHR_9$ or —$NR_9R_{10}$ group if desired oxidized at the nitrogen atom, a nitro group, a phenyl group, an alkyl group of 1 to 4 carbon atoms, a methyl group substituted by an aromatic or saturated heterocyclic group, the heteroatoms being possibly oxidized in the form of N-oxide or S-oxide, $R_4$ represents a —CH(X)—O—C(O)—Y group, in which X and Y represent, independently of each other, an $R_9$ group or a phenyl group, a —$CH_2CH_2$—S—C(O)—W group, in which W represents an $R_9$ group or a phenyl group, $R_5$ represents a hydrogen atom, an alkyl group or an alkenyl group of 1 to 6 carbon atoms, these two latter groups being possibly substituted with:

a hydroxy group or an alcoxy group —OR$_9$,
a phenyl group or a benzyl group,
    a sulfanyl group, an alkylsulfanyl group —SR$_9$ or an alkylsulfanyl group oxidized at the sulfur atom —S(O)R$_9$,
an amino group, an —NHR$_9$ or —NR$_9$R$_{10}$ group, possibly oxidized at the nitrogen atom or,
a guanidino group H$_2$N—C(=NH) —NH—,
a cycloalkyl or cycloalkylmethyl group,
a phenyl group, a benzyl group, which can be substituted at the phenyl group by 1 or 2 of the following substituents:
    a halogen atom,
    a hydroxy group, an alcoxy group —OR$_9$,
    an alkylsulfanyl group —SR$_9$ or an alkylsulfanyl group oxidized at the sulfur atom,
    an amino group or an —NHR$_9$ or —NR$_9$R$_{10}$ group which can be oxidized at the nitrogen atom,
    a nitro group,
    a phenyl group,
    an alkyl group of 1 to 4 carbon atoms,
    a methyl group substituted with a heterocyclic group, the hetero atoms can be oxidized in the form of N-oxide or S-oxide,
R$_6$ and R$_7$ represent independently of each other
    a hydrogen atom,
    an alkyl or alkenyl group of 1 to 6 carbon atoms, which can be substituted with:
        a hydroxy or an alcoxy group —OR$_9$,
        a sulfanyl group, an alkylsulfanyl group —SR$_9$ or an alkylsulfanyl group oxidized at the sulfur atom —S(O)R$_9$,
        an amino group or an alkylamino group —NHR$_9$,
        a guanidino group H$_2$N—C(=NH) —NH—or,
        a carboxy group or an alkyloxycarbonyl group —COOR$_9$,
    a phenyl group, a benzyl group, which can be substituted on the phenyl group by 1 or 2 of the following substituents:
        a halogen atom,
        a phenyl group,
        a hydroxy group or an alcoxy group —OR$_9$,
        an alkylsulfanyl group —SR$_9$ or an alkylsulfanyl group oxidized at the sulfur atom —S(O)R$_9$,
R$_6$ and R$_7$ together represent a saturated or unsaturated cyclic compound of 5 or 6 members, comprising 1 or 2 heteroatoms selected from oxygen, sulfur and nitrogen,
R$_8$ represents,
    an alkyl or alkenyl group of 1 to 6 carbon atoms,
    a phenyl group, a benzyl group,
n is equal to 0 or 1.
Within the scope of the invention, the following terms have the following meanings:
    an alkyl group is a hydrocarbon chain, saturated, linear or branched,
    an alkenyl group is a linear or branched hydrocarbon chain, comprising an unsaturation,
    a cycloalkyl group is a cyclic hydrocarbon chain comprising 3 to 7 carbon atoms,
    a cycloalkylalkyl group is a cycloalkyl group connected to an alkyl group, this alkyl group comprising 1 to 6 carbon atoms,
    a cycloalkylmethyl group is a cycloalkyl group connected to a methyl group,
    a heterocyclic group is a cyclic hydrocarbon chain, aromatic or not, with 5 or 6 members, comprising 1 or 2 heteroatoms selected from atoms of oxygen, sulfur or nitrogen.

Within the scope of the invention, the halogen atoms are preferably chlorine and fluorine.

When a phenyl group is substituted with a phenyl group, it is then preferably in position 4 to form a biphenyl group (also written: (1,1'-biphenyl).

The present invention also has for its object addition salts of pharmacologically acceptable acids of compounds of formula (I) in which R$_1$ and R$_2$ are hydrogen atoms.

A preferred category of compounds according to the invention is that in which the radicals of formula (I) have the following meanings:
    R$_1$ and R$_2$ represent hydrogen atoms,
    n is equal to 0,
    R$_3$ represents
        a hydrogen atom,
        an alkyl group of 1 to 6 atoms of carbon, which can be substituted with a hydroxy group, an alcoxy group —OR$_9$, a sulfanyl group or an alkylsulfanyl group —SR$_9$,
        a phenyl group, a benzyl group which can be substituted on the phenyl group with a halogen atom, an alkyl group of 1 to 4 carbon atoms, a hydroxy group, an alcoxy group —OR$_9$ or an alkylsulfanyl group —SR$_9$,
    R$_4$ represents
        a —CH(X)—O—C(O)—Y group, in which X and Y represent, independently of each other, an R$_9$ group or a phenyl group,
        a —CH$_2$CH$_2$—S—C(O)—W group, in which W represents an R$_9$ group or a phenyl group,
    R$_5$ represents
        a phenyl group, a benzyl group, which can be substituted on the phenyl group with a halogen atom, an alkyl group of 1 to 4 carbon atoms, a hydroxy group, an alcoxy group —OR$_9$ or an alkylsulfanyl group —SR$_9$,
        a biphenylmethyl group,
    R$_6$ represents an alkyl group of 1 to 6 carbon atoms, which can be substituted with a hydroxy group, an alcoxy group —OR$_9$, a sulfanyl group or an alkylsulfanyl group —SR$_9$,
    R$_8$ represents
        an alkyl group of 1 to 6 carbon atoms,
        a phenyl group, a benzyl group.

The compounds of formula (I) can have 1 to 5 chiral atoms on the skeleton and if desired 1 to 3 chiral atoms on the different groups of R$_3$ to R$_9$. The compounds of the invention can exist in different isomeric forms including the form of an enantiomers and diastereoisomers. The present invention comprises these different forms as well as their mixtures, including racemic mixtures.

The carbon bearing the R$_6$ radical, when R$_6$ is different from the hydrogen atom, is preferably of the absolute configuration (S).

The compounds of the invention of formula (I) can be prepared according to the processes described in annexes 1, 2 and 3.

In the description of the process, the radicals A$_1$ and A$_2$ have the following meanings:
    A$_1$ represents a biphenylmethyl group, a tert-butoxycarbonyl group (Boc), a benzyloxycarbonyl group (Bzc or Z) or a fluorenylmethoxycarbonyl group (Fmoc),
    A$_2$ represents a tert-butoxycarbonyl group (Boc) or a fluorenylmethoxycarbonyl group (Fmoc).

tBu represents a tert-butyl group and Bn represents a benzyl group.

The compounds of formula (Ia) and (Ib), which are compounds of the formula (I) according to the invention, are prepared according to the process represented in annex 1. $R_3$, $R_4$, $R_5$, $R_6$, $R_7$, $R_8$, R', R" and n have the meanings given in formula (I). According to this process, a derivative of hydroxyphosphinylpropanoic acid of formula (IVb) is reacted with an amino acid derivative of formula (V), in the presence of benzotriazole-1-yloxy-tris(dimethylamino) phosphonium hexafluorophosphate (BOP) or else of 1-ethyl-3-(3-dimethylaminopropyl)carbodiimide methiodide (EDC), in an organic solvent such as dimethylformamide. The compound of formula (V) can be used in the form of a salt, such as the salt of p-toluenesulfonic acid. It is then particularly advantageous to work in the presence of a base such as a tertiary amine such as diisopropylethylamine. This reaction permits obtaining a compound of formula (III).

The compound of formula (III) is used to prepare the compound of formula (II), in which the three amine, phosphinate and carboxylate functions are protected simultaneously. The compound of formula (III) can be treated in an organic solvent such as tetrahydrofuran, with an alcohol of the formula $R_4OH$, in the presence of N,N'-dicyclohexylcarbodiimide (DCC) and 4-dimethylaminopyridine (DMAP) to obtain the compound of formula (II).

Alternatively, the compound of formula (III) can be transformed into the cesium salt by the action of cesium A carbonate. This obtained salt can then be treated, in an organic solvent such as dimethylformamide (DMF), with a halogenated derivative $R_4Z$, in which Z represents a halogen atom such as bromine, chlorine or iodine, to obtain the compound of formula (II).

To prepare the compound of formula (Ia), the protective group of the amine function is removed. If $A_2$ is a tert-butoxycarbonyl group, the removal of the protective group can be carried out in a weak acid medium, such as formic acid. If $A_2$ is a fluorenylmethoxycarbonyl group, the removal of the protective group can be carried out in a basic medium such as piperidine.

To prepare the compound of formula (Ib), a ketone R'(R")C=O is condensed on a compound of formula (Ia), these R'(R")C=O ketones being obtained by Fries rearrangement of the corresponding R"CO$_2$R' esters.

The compounds of formula (V), in which n can be equal to 0 or 1, $R_6$, $R_7$ and $R_8$ have one of the meanings given in formula (I), represent an α or a β amino acid which is natural or not. They can be synthesized according to conventional methods well known to those skilled in the art.

The compounds of formula (IVb) can be prepared according to the processes described in annexes 2 and 3.

According to diagram 1, annex 2, a derivative of phosphinic acid of formula (VIII) is added to a derivative of acrylic ester of formula (VII), in the presence of N,O-bis trimethylsilyl acetamide, without a solvent or in an inert organic solvent such as acetonitrile, to obtain the compound of formula (VI). If $A_1$ is a biphenyl methyl or benzyloxycarbonyl group, removal of a protective group in bromohydric acid medium exposes the amine function which is then reprotected by a tert-butoxycarbonyle group or a fluorentylmethoxycarbonyle group according to processes well known to those in the art, to obtain the compound of formula (IVa). obtaining the compound of formula (IVb) from the compound of formula (IVa) is a conventional saponification or hydrolysis in acid medium.

In the case in which $R_5$ represents the final product of formula (I), a biphenylmethyl group, there is used, according to a modification, a compound of formula (VI), in which the radical $R_5$ represents first of all a 4-bromophenyl methyl group. This obtained compound is reacted with phenylboronic acid in a solvent, such as a toluene/methanol mixture, and in the presence of tetrakis triphenylphosphine palladium and sodium carbonate to obtain the compound of formula (VI), in which $R_5$ is a biphenylmethyl group.

The compound of formula (VIII) is obtained by indirect or direct synthesis, represented in diagram 2 of annex 2:

by the indirect route, the process consists in treating the diphenylmethylamine with phosphonous acid and is reacting the obtained phosphonous acid salt of diphenylmethylamine, with an aldehyde $R_3CHO$ in anhydrous ethanol to obtain a compound of formula (IX). The amine function of this compound of formula (IX) is if desired then subjected to removal of its protective group in water acidified with a mineral acid, such as hydrochloric acid or bromohydric acid, then the obtained compound is treated with propylene oxide and finally acylated to obtain a compound of formula (VIII), by the direct route, the process consists in treating the diphenylmethylamine chlorohydrate with phosphonous acid and an aldehyde $R_3CHO$, this reaction being carried out in a mixture of ethanol with water with reflux.

The compounds of formula (VII) can be obtained by two methods, which are represented in annex 3, respectively in diagrams 3 and 4:

according to the first process (diagram 3), a halide, preferably a bromide, of alkyl or aralkyl $R_5Z$ is erected with the triethylphosphonoacetate, in the presence of sodium hydride, to obtain the compound of formula (X), which is reacted with formaldehyde, in the presence of potassium carbonate, to obtain a compound of formula (VII).

according to the second process (diagram 4), there are obtained compounds of formula (VII) by a Mannich reaction on a monoester of a malonic acid of formula (XI).

The compounds of general formula (I), thus obtained, are in the form of isomers, including in the form of enantiomers, diastereoisomers and mixtures of these different forms, including racemic mixtures.

The compounds of formula (I), optically pure, can be obtained by separation with semi-preparative HPLC (Chromasil $C_8$, 10 mm, 20×250 mm, acetonitrile-water, 15 ml/min).

The compounds of formula (I), optically pure, can also be obtained by resolution from a chiral amine and from the derivative of phosphinic acid to formula (VIII), then if desired by Michael diastereoselective addition, in the presence of chiral inductors, which lead to compounds of formula (VI), which have a perfectly defined stereochemistry.

The compounds of formula (I), optically pure, can finally be obtained by resolution or by enzymatic resolution of the synthesis intermediaries (VI), (IVa) or (IVb).

The separations envisaged above can be carried out on a semi-preparative column of Chromasil $C_8$, (10 mm, 20×250 mm, 15 ml/min) with an acetonitrile/water mixture.

The following examples have for their object to illustrate the preparation of several compounds of the invention. The elementary analyses and the NMR spectra confirm the structures of the obtained compounds.

In the names of the compounds, the "—" forms a part of the word, and the "_" serves only to show a break at the end of the line; if there is no break in the end of the line, it is to be omitted and not replaced by a normal dash nor by a space.

In the following examples, the amino acids used during these syntheses have an absolute configuration (S).

As to the nomenclature of the compounds described in the examples which follow, according to convention, there is not indicated the configuration of the phosphorus.

EXAMPLE 1

Formiate of(R,S)-N-[3-[[2-(acetylthio)ethoxyl( 1-aminoethyl)phosnhinyl-2-([1,1'-biphenyl-4-ylmethyl) -1-oxopropyl]-L-alaninate of phenylmethyle 1.1 Ethyl 4-bromo-α-(diethoxyphosphinyl) benzenepropanoate To a solution of 9 ml (45.4 mmol) of triethylphosphonoacetate in 14 ml of dimethylformamide, there is added, at −10° C., 1.5 g (49.9 mmol) of 80% sodium hydride. After 15 minutes, there is added dropwise 11.8 g (47.3 mmol) of 4-bromophenyl methyl bromide. The reaction mixture is brought to a temperature of about 20° C. and agitated at this temperature overnight. The solvent is evaporated under reduced pressure. The residue is collected in ethyl acetate, washed with water, dried with sodium sulfate and filtered. The solvent is evaporated under reduced pressure. The residue is purified by a chromatography on silica gel by eluting with a heptane/ethyle acetate mixture: 1/4. 7.8 g of product is recovered in the form of an oil. (yield=43.7%).

1.2. Ethyl 4-bromo-α-methylenebenzenepropanoate

A mixture of 5.5 g (14 mmol) of ethyl 4-bromo-α-diethoxyphosphinyl benzenepropanoate, 5.3 ml (71 mmol) of formaldehyde and of 5.8 g (41.8 mmol) of potassium carbonate is refluxed for 3 hours. There is added a mixture of water and diethyl ether. The aqueous phase is removed with diethyl ether. The assembly of the organic phases is washed with water, dried on sodium sulfate, filtered and evaporated under reduced pressure. The residue is distilled under reduced pressure.

There is recovered 6.7 g of product in the form of an oil. (yield=75%).

1.3. [1-[diphenylmethyl)amino]ethyl]phosphinic acid

A solution of 10 g (45.5 mmol) of diphenylmethylamine chlorhydrate and 4.8 ml (46.3 mmol) of 50% hypophosphonic acid in water in 100 ml of a water/ethanol mixture: 90/10, is refluxed. There is added dropwise 4 g (0.09 mmol) of acetaldehyde. After addition, reflux is maintained for one hour. The obtained precipitate is filtered and washed with 100 ml of water and 100 ml of acetone. There are recovered 8 g of product (yield=64%).

Melting point: 236° C.

1.4. (1-aminoethyl)phosphinic acid

A mixture of 4.5 g (16.4 mmol) of 1-diphenylmethyl amino ethyl phosphinic acid and 30 ml of 6N hydrochloric acid is refluxed for 2 hours. Two phases appear. The mixture is dried by evaporation under vacuum while hot, then admixed with 30 ml of water. The aqueous phase is washed three times with diethyl ether. The aqueous phase, again evaporated, gives l-aminoethyl phosphinic acid chlorhydrate, which is mixed with 15 ml of absolute ethanol. 8 ml of propylene oxide is added dropwise, with agitation, at 0° C. There is observed the formation of an abundant white precipitate, which is filtered and washed with diethyl ether.

There is recovered 1.7 g of product (yield=95.3%).

Melting point: 222–224° C. (decomposition).

1.5. [1-[[(phenylmethoxy)carbonyl]amino]ethyl] phosphinic acid

To a solution of 1.7 g (15.6 mmol) of 1-aminoethyl phosphinic acid in 35 ml of a mixture of dioxane and water, in the presence of an equivalent of soda (624 mg), there is added, 0° C., dropwise and simultaneously, a solution of 3.1 g (18.3 mmol) of benzyl chloroformate in 9 ml of dioxane and, so as to maintain the pH of the reaction about 9, a solution of 1 g of soda in 8.7 ml of water. At the end of the addition, the mixture is maintained at a temperature about 20° C. for 2 hours. The aqueous phase is then washed 3 times with 20 ml of diethyl ether. The aqueous phase is acidified, at 0° C., with brisk agitation, with 11 ml of a 6N hydrochloric acid solution. An abundant white precipitate forms, which is filtered, washed with water and dried. There is recovered 2.8 g of product (yield=73.9%).

Melting point: 132–1340° C.

1.6. (R)-[1-[[(phenylmethoxy)carbonyl]amino])ethyl] phosphinic acid

To a solution of 13.2 g (54.3 mmol) of 1-phenylmethoxy carbonyl amino ethyl phosphinic acid in 45 ml of methanol with reflux, there is added dropwise a solution of 7 ml (54.3 mmol) of D+α-methylbenzylamine in 3 ml of methanol. The solvent is distilled under reduced pressure. The residue is recrystallized 3 times in a mixture of ethyl acetate and isopropanol.

There is recovered 6.2 9 of salt.

To 6.2 g of this salt is added, at ambient temperature, 51 ml of 1N hydrochloric acid. After 15 minutes, the aqueous phase is extracted with ethyl acetate. The combination of the organic phases is washed with water, dried on sodium sulfate, filtered and evaporated under reduced pressure.

There is recovered 4 g of product in the form of a white solid (yield=60.6%).

Melting point: 134° C.

$[\alpha]^{20}_D$=−45°(c=1, ethanol)

1.7. Ethyl (R)-3-(4-bromophenyl)-2-[[hydroxy[1-[[phenylmethoxy)carbonyl]amino]ethyl]phosphinyl] methyl]propanoate A solution of 2.9 g (11.9 mmol) of (R)-[1-[[(phenylmethoxy)carbonyl]amino]ethyl]phosphinic acid, 3.5 g (13 mmol) of ethyl 4-bromo-α-methylenebenzenepropanoate and 6.2 ml of N,O-bis (trimethylsilyl)acetamide is maintained at 60° C. for 24 hours. After cooling, 60 ml of a mixture of ethyl acetate and water (1:1 by volume) is added. The aqueous phase is extracted with ethyl acetate. The combination of the organic phases is washed with water, dried on sodium sulfate, filtered and evaporated under vacuum. It is purified by recrystallization in a mixture of ethyl acetate and hexane.

There is recovered 5.8 g of product (yield=94.9%).

Melting point: 128–130° C.

Retention time on HPLC (Kromasil column, 5 μm, 10×250 mm, acetonitrile-water, 60%, 1 ml/min)=6.4 and 6.6 min.

1.8. Ethyl (R)-3-([1,1'-biphenyl]-4-yl)-2-[[hydroxy[1-[[(phenylmethoxy)carbonyl]aamino]ethyl]phosphinyl] methyl]propanoate 6.4 g (12.5 mmol) of ethyl (R)-3-(4-bromophenyl)-2-[[hydroxy[1-[[(phenylmethoxy)carbonyl]amino])ethyl] phosphinyl]methyl]propanoate is condensed with 1.54 g (12.6 mmol) of phenylboronic acid in 48 ml of a toluene/ methanol mixture: 2/1, of tetrakis(triphenylphosphine) palladium and of 12.8 ml of 2M sodium carbonate. The reaction mixture is agitated for 6 hours under nitrogen and with reflux. After cooling, there is added 50 ml of ethyl acetate and it is acidified to pH=3 with an aqueous 2N hydrochloric acid solution. After filtration on celite, and rinsing with ethyl acetate, the solvent is evaporated under reduced pressure. It is purified by chromatography on silica gel by eluding with a dichloromethane/methanol/acetic acid mixture: 9/1/0.4 mixture.

There is recovered 5.3 g of product (yield=83.5%).

Melting point: 124–126° C.

Retention time on HPLC (Kromasil column, 5 µm, 10×250 mm, acetonitrile-water, 60%, 1 ml/min)=8.0 and 8.2 min.

1.9. Ethyl (R)-3-([1,1'-biphenyl]-4-yl)-2-[[[1-[[(1,1-dimethylethoxy)carbonyl]amino]ethyl]hydroxyphosphinyl]methyl]propanoate To 10 ml of a 33% solution of hydrobromic acid in acetic acid, cooled to 0° C., there is added 4.7 g (9.2 mmol) of ethyl (R)-3-([1,1'-biphenyl[-4-yl)-2-[hydroxy[1-[[(phenylmethoxy)carbonyl]amino]ethyl]phosphiny]methyl]propanoate. The mixture is then agitated, at ambient temperature, for 30 minutes. The solvent is evaporated under reduced pressure. The residue is gathered in toluene then the cyclohexane is evaporated, under reduced pressure, to dryness.

There is recovered 4.2 g of bromhydrate of ethyl (R)-3-([1,1'-biphenyl]-4-yl)-2-[[hydroxy[1-[[(phenylmethoxy)carbonyl]amino]ethyl]phosphinyl]methyl]propanoate.

To a solution of 4.2 g (9.2 mmol) of this salt in 15 ml of dimethylformamide, is added dropwise 5.1 ml of triethylamine (36.7 mmol) and 2 g (9.2. mmol) of di-tert-butyldicarbonate. At the end of the addition, the mixture is maintained at a temperature of about 20° C. overnight. The solvent is concentrated. There is added 15 ml of water and it is acidified to pH=3 with a 2N hydrochloric acid solution. The aqueous phase is extracted with ethyl acetate. The combination of the organic phases is washed with water, dried on sodium sulfate, filtered and evaporated under vacuum. It is purified by chromatography on silica gel by eluting with a dichloromethane/methanol/acetic acid: 9/1/0.4 mixture.

There is recovered 3.6 g of product (yield=82%).

Melting point: 114–116° C.

Retention time on HPLC (Kromasil column, 5 µm, 10×250 mm, acetonitrile-water, 60%, 1 ml/min)=8.4 and 8.7 min.

1.10. (R)-3-([1,1'-biphenyl]-4-yl)-2-[[[1-[[(1,1-dimethylethoxy)carbonyl]amino]ethyl]hydroxyphosphinyl]methyl]propanoic acid To a solution of 3.6 g (7.6 mmol) of ethyl (R)-3-([1,1'-biphenyl]-4-yl)-2-[[[1-[[(1,1-dimethylethoxy)carbonyl]amino]ethyl]hydroxyphosphinyl]methyl propanoate in 35 ml of ethanol, is added 60 ml of 1N lithium hydroxide. After 24 hours of agitation, the medium is acidified with 3N hydrochloric acid. The ethanol is then evaporated and it is extracted three times with ethyl acetate. The combination of the organic phases is washed with water, dried on sodium sulfate and evaporated.

There is recovered 3.35 g of product (yield=99%).

Melting point: 110° C. (decomposition),

Retention time on HPLC (Kromasil column, 5 µm, 10×250 mm, acetonitrile-water, 60%, 1 ml/min)=5.0 and 5.1 min.

1.11. Phenylmethyl (R,S)-N-[2-([1,1'-biphenyl-4-ylmethyl)-3-[[(1-[[1,1-dimethlethoxy)carbonyl]amino]ethyl]hydroxyphosphinyl]-1-oxopropyl]-L-alaninate (isomer A (R,S,S) and isomer B (R,R,S))

To 3.4 g (7.5 mmol) of (R)-3-([1,1'-biphenyl]-4-yl) -2-[[[1-[[(1,1-dimethylethoxy)carbonyl]amino]ethyl]hydroxyphosphinyl]methyl]propanoic acid, 1.4 g (7.5 mmol) of phenylmethyl L-alaninate in the form of chlorhydrate and 6.8 g (15.1 mmol) of benzotriazol-1-yl-oxy-tris (dimethylamino)phosphonium hexafluorophosphate (BOP) in 12 ml of dimethylformamide, is added with agitation at a temperature of about 20° C., 13 ml of diisopropylethylamine. After 30 minutes of reaction at this temperature, the dimethylformamide is evaporated under reduced pressure, 50 ml of ethyl acetate is added, and it is acidified to pH=3 with a 2N aqueous solution of hydrochloric acid. The aqueous phase is extracted with ethyl acetate. The combination of the organic phases is washed with water, dried on sodium sulfate, filtered and evaporated under vacuum. It is purified by chromatography on silica gel by eluting with dichloromethane/methanol/acetic acid: 9/1/0.3 mixture.

There is recovered 1 g of isomer A (23.3%) and 1.1 g of isomer B (25.6%).

Retention time on HPLC (Kromasil column 5 µm, 10×250 mm, acetonitrile-water: 60%, 1 ml/min)=14.1 and 15.5 min.

1.12. S-(2 hydroxyethyl)ethanethioate

To a solution of 8.2 g (107.7 mmol) of thioacetic acid in 43 ml of toluene, is added, at 0° C., 16.4 g (107.7 mmol) of 1.8-diazabicyclo[5.4.0]undec-7-ene and 16.1 g (93.7 mmol) of 2-iodoethanol. The mixture is maintained at a temperature of about 20° C. for 3 hours. There is added a mixture of ethyl acetate and water. The organic phase is washed with water, dried on sodium sulfate, filtered and evaporated under vacuum. The residue is taken up with ether, filtered and evaporated under reduced pressure.

There is recovered 7.98 g of product (yield=71%).

1.13. Phenylmethyl (R, S)-N-[3-[[2-(Acethylthio)ethoxy][1-[[(1,1-dimethylethoxy)carbonyl]amino]ethyl]phosphinyl]-2-([1,1'-biphenyl]-4-ylmethyl)-1-oxopropyl]-L-alaninate To a solution of 100 mg (0.17 mmol) of phenylmethyl (R, S)-N-[2-([1,1'-biphenyl]-4-ylmethyl)-3[[(1-[[(1,1-dimethylethoxy)carbony]amino]ethyl]hydroxyphosphinyl]-1-oxopropyl]-L-alaninate (isomer A), in 10 ml of anhydrous tetrahydrofuran, is added 103 mg of S-(2-hydroxyethyl) ethanethioate (0.87 mmol), 32 mg of dimethylaminopyridine (0.26 mmol) and 179 mg of dicyclohexylcarbamidine (0.87 mmol). The mixture is maintained at a temperature of about 20° C. for 2 days. After filtration, the filtrate is evaporated under reduced pressure. The residue is taken up in ethyl acetate, filtered and evaporated under reduced pressure. It is purified by chromatography on silica gel by eluting with a dichloromethane/methanol: 40/3 mixture.

There is recovered 78 mg of product (yield=66.4%).

Melting point: 78–80° C.

Retention time on HPLC (Kromasil column 5 µm, 10×250 mm, acetonitrile-water: 70%, 1 ml/min)=8.7 min.

1.14. Phenylmethyl (R,S)-N-[3-[[2-(acetylthio)ethoxy](1-aminoethyl)phosphinyl]-2-([1,1'-biphenyl]-4-ylmethyl)-1-oxopropyl]-L-alaninate formiate A solution of 78 mg (0.12 mmol) of phenylmethyl (R,S)-N-[3-[[2-(acetylthio)ethoxy][1-[[(1,1-dimethylethoxy)carbonyl]amino]ethyl]phosphinyl]-2-([1,1[-biphenyl]-4-ylmethyl)-1-oxopropyl]-L-alaninate in 1 ml of formic acid is maintained under agitation at a temperature of about 20° C.

for 4 hours. The solvent is evaporated under reduced pressure to dryness. The residue is purified by preparative chromatography (Kromasil $C_8$, 10 mm, 20×250 mm, acetonitrile/water: 50/50, 15 ml/min).

There is recovered 71.8 mg of product (yield=82%).

Melting point: 108–110° C.

Retention time on HPLC (Kromasil column, 5 μm, 10×250 mm, acetonitrile/water: 50%, 1 ml/min): 6.4 and 6.9 min.

EXAMPLE 2

Phenylmethyl (R,S)-N-[3-[[1-acetyloxy-2-methylpropoxy](1-aminoethyl)phosphinyl]-2-([1,1'-biphenyl]-4-ylmethyl)-1-oxoyropyl]-L-alaninate formiate 2.1. 1-bromo-2-methylpropyl acetate To a solution of 13.6 g (0.1 mol) of acetyl bromide in 60 ml of anhydrous dichloromethane, is added 1 g of zinc chloride, and dropwise, 9.1 ml (0.1 mol) of isobutyraldehyde, so as to maintain the temperature of the reaction below −5° C. After these additions, the mixture is maintained at this temperature for 2 hours. It is then filtered on basic alumina, then rinsed with 20 ml of anhydrous dichloromethane. The solvent is evaporated under reduced pressure. The residue is taken up in ether, washed with water, dried on sodium sulfate and filtered. The solvent is evaporated under vacuum.

There is recovered 16.2 g of product (yield=83%).

2.2. Phenylmethyl (R,S)-N-[3-[[1-(acetyloxy)-2-methylpropoxy][1-[[(1,1-dimethylethoxy)carbonyl]amino]ethyl]phosphinyl]-2-([1,1'-biphenyl]-4-ylmethyl)-1-oxopropyl]-L-alaninate To a solution of 118 mg (0.21 mmol) of phenylmethyl (R,S)-N-[2-([1,1'-biphenyl]-4-ylmethyl)-3-[[(1-[[(1,1-dimethylethoxy)carbonyl]amino]ethyl]hydroxyphosphinyl]-1-oxopropyl]-L-alaninate (isomer A) in a mixture of 1.4 ml of methanol and of 0.14 ml of water, there is added 16.7t of cesium carbonate to a pH of 8–9. The solvent is evaporated under reduced pressure, to dryness. The solid in the form of the cesium salt is dissolved in 1.4 ml of dimethylformamide. 200 mg (1 mmol) of 1-bromo-2-methylpropyl acetate is added. The mixture is maintained at a temperature of about 20° C. overnight. There is added to it a mixture of ethyl acetate and water. The organic phase is washed with water, dried on sodium sulfate, filtered and evaporated under vacuum.

There is recovered 59 mg of product (yield=41.7%).

Melting point: 76–78° C.

Retention time on HPLC (Kromasil column 5 μm, 10×250 mm, acetonitrile-water: 70%, 1 ml/min)=11.5; 12.4 and 13.2 min.

2.3. Formiate of phenylmethyl (R,S)-N-[3-[[1'-acetyloxy)-2-methylpropoxy](1-aminoethyl)phosphinyl]-2-([1,1-biphenyl]-4-ylmethyl)-1-oxopropyl]-L-alaninate The process is conducted according to the operative conditions described in 1.12. from 58 mg (0.08 mmol) of phenylmethyl (R,S)-N-[3-[[1-(acetyloxy)-2-methylpropoxy][1[[(1,1-dimethylethoxy)carbonyl]amino]ethyl]phosphinyl]-2-([1,1'-biphenyl]-4-ylmethyl)-1-oxopropyl]-L-alaninate and 0.7 ml of formic acid.

32 mg of product are recovered (yield=60%).

Melting point: 120–122° C.

Retention time on HPLC (Kromasil column 5 μm, 10×250 mm, acetonitrile-water: 50%, 1 ml/min)=7.1, 8.3 and 9.6 min.

EXAMPLE 3

Formiate of phenylmethyl (R,S)-N-[3-[[2-(acetylthio)ethoxy](aminophenylmethyl)phosphinyl]-2-([1,1'-biphenyl]-4-ylmethyl)-1-oxopronyl]-L-alaninate 3.1. α-phenylbenzenemethanamine phosphinate To a solution of 33.1 g (0.5 mol) of 100% phosphonous acid in 120 ml of anhydrous ethanol; cooled to 0° C., is added dropwise 91.9 g (0.5 mol) of diphenylmethylamine taking care that the temperature does not exceed 25° C. A white precipitate forms after this addition, to which is added 200 ml of diethyl ether. The precipitate is filtered, rinsed with diethyl ether, then dried.

There is recovered 119.4 g of product (yield=95.6%).

Melting point: 176–177° C.

3.2. [[(Diphenylmethyl)amino]phenylmethyl]phosphinic acid

A solution of 110 g (0.44 mol) of α-phenylbenzenemethanamine phosphinate in 310 ml of anhydrous ethanol is refluxed. 89.5 ml (0.88 mol) of benzaldehyde in 102 ml of anhydrous ethanol are added dropwise. An abundant white precipitate forms. After addition, reflux is continued for 2.5 hours. After cooling, there is added 840 ml of acetone. The obtained precipitate is filtered and washed with the same solvent.

There is recovered 75.3 g of product (yield=50.6%).

Melting point: 212° C. 3.3. (Aminophenylmethyl)phosphinic acid

A mixture of 75 g (0.22 mol) of [[diphenylmethyl)amino]phenylmethyl]phosphinic acid and 509 ml of 48% aqueous hydrobromic acid is refluxed for 2 hours. Two phases appear. The mixture is dried by evaporation under vacuum while hot, then taken up in 94 ml of water. The aqueous phase is washed three-times with diethyl ether. The aqueous phase, again evaporated, gives the bromhydrate of the (aminophenylmethyl)phosphinic acid, which is taken up in 340 ml of absolute ethanol. There is added 108 ml of propylene oxide, dropwise, with agitation, at 0° C. There is observed the formation of an abundant white precipitate 15 which is filtered and washed with diethyl ether. There is recovered 36 g of product (yield=94.6%).

Melting point: 243° C.

3.4. [[[(Phenylmethoxy)carbonyl]amino]phenylmethyl]phosphinic acid

The process is conducted according to the operative conditions described in 1.5., starting from 10 g (58.5 mmol) of aminophenylmethyl phosphinic acid and 9.8. ml (68.6 rmnol) of phenylmethyl chloroformiate.

There is recovered 17.78 g of product (yield=99.7%).

Melting point: 143° C.

3.5. (R)-[[[(phenylmethoxy)carbony]amino]phenylmethyl]phosphinic acid

The operative conditions described in 1.6. are followed, starting with 9.2 g (21.6 mmol) of [[[(phenylmethoxy)carbonyl]amino]phenylmethyl]phosphinic acid.

There is recovered 3.6 g of product (yield=77.8%).

Melting point: 160° C.

$[\alpha]^{20}_D$=+2.8°(c=1, ethanol).

3.6. Ethyl (R)-3-(4-bromophenyl)-2[[hydroxy[[[(phenylmethoxy)carbonyl]amino]methyl]phosphinyl]methyl]propanoate The operative conditions described in 1.7. are followed, starting with 15.7 g (51.4 mmol) of (R)-[[[(phenylmethoxy)carbonyl]amino]phenylmethyl]phosphinic acid and 16.6 g (61.7 mmol) of ethyl 4-bromo-α-methylenebenzenepropanoate.

There is recovered 25.8 g of product (yield=87.4%).

Melting point: 120–122° C.

Retention time on HPLC (Kromasil column 5 μm, 10×250 mm, acetonitrile-water: 60%, 1 ml/min)=6.5 and 6.6 min.

3.7. Ethyl (R)-3-[1,1'=biphenyl)-4-yl-2-[[hydroxy [[[(phenylmethoxy)carbonyl]amino]methyl]phosphinyl] methyl]propanoate The operative conditions described in 1.8. are followed, starting with 25 g (43.6 mmol) of ethyl (R)-3-(4-bromophenyl)-2[[hydroxy[[[(phenylmethoxy)carbonyl] amino]methyl]phosphinyl]methyl]propanoate and 5.4 g (43.8 mmol) of phenylboronic acid.

There is recovered 21.7 g of product (yield=87.3%).

Melting point: 116–118° C.

Retention time on HPLC (Kromasil column 5 μm, 10×250 mm, acetonitrile-water: 60%, 1 ml/min)=9.6 et 9.8 min.

3.8. Ethyl (R)-3-[1,1'-biphenyl]-4-yl-2[[[[[(1,1-dimethylethoxy carbonyl]amino]methyl] hydroxyphosphinyl]methyl]propanoate The operative conditions described in 1.9. are followed, starting with 15 g (26.3 mmol) of ethyl (R)-3-[1,1'-biphenyl]-4-yl-2 [[hydroxy[[[(phenylmethoxy)carbonyl] amino]methyl]phosphinyl]methyl]propanoate.

There is recovered 11.2 g of product (yield=79.58).

Melting point: 110–112° C.

Retention time on HPLC (Kromasil column) 5 μm, 10×250 mm, acetonitrile-water: 60%, 1 ml/min)=12.0 min.

3.9. (R)-3-[1,1'-biphenyl]-4-yl-2[[[[[(1,1-dimethyl ethoxy)carbonyl]amino]methyl]hydroxyphosphinyl] methyl]propanoic acid The operative conditions described in 1.10. are followed, starting with 11.2 g (20.9 mmol) of ethyl (R)3-[1,1 '-biphenyl]-4-yl-2[[[[[(1,1-dimethylethoxy)carbonyl]amino] methyl]hydroxyphosphiny]methyl]propanoate.

There is recovered 10.5 g of product (yield=99%).

Melting point: 120° C. (decomposition).

Retention time on HPLC (Kromasil column 5 μm, 10×250 mm, acetonitrile-water: 60%, 1 ml/min)=6.7 min.

3.10. Phenylmethyl (R,S)-N-[3-([1,1-biphenyl]-4-yl)-2-[[[[[(1,1-dimethylethoxy)carbonyl]amino]phenylmethyl] hydroxyphosphinyl]methyl]-1-oxopropyl]-L-alaninate The operative conditions described in 1.11. are followed, starting from 5 g (9.84 mmol) of (R)-3-[1,1'-biphenyl]-4-yl-2[[[[[(1,1-dimethylethoxy)carbonyl]amino]methyl] hydroxyphosphinyl]methyl]propanoic acid and 1.8 g (9.9 mmol) of phenylmethyl L-alaninate in the form of chlorhydrate. There is recovered 1.3 g (20.7%) of isomer A and 1.8 g (28.7%) of isomer B.

Melting point: 143–146° C.

Retention time on HPLC (Kromasil column 5 μm, 10×250 mm, acetonitrile-water: 60%, 1 ml/min)=13.7 and 15.2 min.

3.11. Phenylmethyl (R, S)-N-[3-[[2-(acetylthio)ethoxy] [[[1,1-dimethylethoxy)carbonyl]amino]phenylmethyl] hydroxyphosphinyl]-2-([1,1'-biphenyl]-4-ylmethyl)-1-oxopropyl]-L-alaninate The operative conditions described in 1.13. are followed, starting with 210 mg (0.33 mmol) of phenylmethyl (R, S)-N-[3-([1,1'-biphenyl]-4-yl)-2-[[[[[(1,1-dimethylethoxy) carbonyl]amino]phenylmethyl]hydroxyphosphinyl] methyl]-1-oxopropyl]-L-alaninate and 195 mg (1.65 mmol) of S-(2-hydroxyethyl) ethanethioate.

There is recovered 169 mg of product (yield=69.6%).

Melting point: 102–104° C.

Retention time on HPLC (Kromasil column 5 μm, 10×250 mm, acetonitrile-water: 70%, 1 ml/min)=12.3 min.

3.12. Formiate of phenylmethyl (R,S)-N-[3-[[(2-(acetylthio)ethoxy](aminophenylmethyl)phosphinyl]-2-([1,1'-biphenyl]-4-ylmethyl)-1-oxopropyl]-L-alaninate The operative conditions described in 1.14. are followed, starting with 132 mg (0.18 mmol) of phenylmethyl (R,S)-N-[3-[[2-(acethylthio)ethoxy][[[(1,1-dimethylethoxy) carbonyl]amino]phenylmethyl]hydroxyphosphinyl]-2-((1, 1'-biphenyl]-4-ylmethyl)-1-oxopropyl]-L-alaninate and 1.4 ml of formic acid.

There is recovered 83 mg of product (yield=67.9%).

Melting point: 110–112° C.

Retention time on HPLC (Kromasil column 5 μm, 10×250 mm, acetonitrile-water: 50%, 1 ml/min)=9.2 and 10.2 min.

EXAMPLE 4

Formiate of phenylmethyl (R,S)-N-[3-[[1-(acetyloxy)-2-methylprooxyl](aminophenylmethyl) phosphinyl]-2-([1,1'-biphenyl]-4-ylmethyl)-1-oxopropyl]-L-alaninate 4.1. Phenylmethyl (R,S)-N-[3-[[1-acetyloxy)-2-methylpropoxyl][[[(1,1-dimethylethoxy)carbonyl]amino] phenylmethyl]phosphinyl]-2-([1,1'-biphenyl]-4-ylmethyl)-1-oxopropyl]-L-alaninate The operative conditions described in 1.13. are followed, starting from 100 mg (0.16 mmol) of phenylmethyl (R, S)-N-[3-([1,1'-biphenyl-4-yl)-2-[[[[[(1,1-dimethylethoxy) carbonyl]amino]phenylmethyl]hydroxyphosphiny]methyl]-1-oxopropyl]-L-alaninate and 153 mg (0.78 mmol) of 1-bromo-2-methylpropyl acetate.

There is recovered 36 mg of product (yield=31%).

Melting point: 80–82° C.

Retention time on HPLC (Kromasil column 5 μm, 10×250 mm, acenotrile-water: 70%, 1 ml/min)=18.3; 19.6 and 21.5 min.

4.2. Formiate of phenylmethyl (R, S)-N-[3-[[1-(acetyloxy)-2-methylpropoxy](aminophenylmethyl, phosphinyl]-2-([1,1'-biphenyl]-4-ylmethyl)-1-oxopropyl]-L-alaninate The operative conditions described in 1.14. are followed, starting from 35 mg (0.047 mmol) of phenylmethyl (R,S)-N-[3-[[1-(acetyloxy)-2-methylpropoxy][[[1,1-dimethylethoxy) carbonyl]amino]phenylmethyl] phosphinyl]-2-([1,1'-biphenyl]-4-ylmethyl)-1-oxopropyl]-L-alaninate and 0.4 ml of formic acid.

There is recovered 19.5 mg of product (yield=60%).

Melting point: 132–134° C.

Retention time on HPLC (Kromasil column 5 μm, 10×250 mm, acetonitrile-water: 50%, 1 ml/min)=8.5; 12.2 and 15.0 min.

To synthesize the compounds of formula (I) of another configuration, the same procedure is followed, starting with intermediates having the desired configuration.

The following table illustrates several compounds of the invention, as well as their physical characteristics.

When n is equal to one in this table, $R_7$ represents a hydrogen atom.

Moreover, the phosphorus is a chiral center and the $R_4$ group can also comprise one or several chiral centers. Because of this, when the chiral centers of the skeleton are resolved, is as in the examples, there is obtained a mixture of enantioners or of diastereoisomers. According to the convention, these are called 1, 2, 3 etc . . . by order of increasing retention time under the conditions of chromatography described in the text.

TABLE $$\underset{R_1}{R_1}\underset{|}{N}-\underset{R_2}{\overset{R_3}{\underset{|}{C}}}-\overset{O}{\underset{||}{P}}(OR_4)-\text{...}-CONH-CH(R_5)-C(R_6)(R_7)-(\,)_n COOR_8 \quad (I)$$

| No. | $R_1$ | $R_2$ | $R_3$ | $R_4$ | $R_5$ | $R_6$ | $R_8$ | n | M.P. (°C.) | Tr (min) % acetonitrile |
|---|---|---|---|---|---|---|---|---|---|---|
| 1 | H | H | —CH$_3$ | —CH$_2$CH$_2$SCOCH$_3$ | 4-biphenylmethyl | —CH$_3$ | benzyl | 0 | 108–110 (HCO$_2$H) | 1:6.4 2:6.9 50% |
| 2 | H | H | —CH$_3$ | —CHOCOCH$_3$ \| CH$_3$ | 4-biphenylmethyl | —CH$_3$ | benzyl | 0 | 120–122 (HCO$_2$H) | 1:7.1 2:8.3 3:9.6 50% |
| 3 | H | H | phenyl | —CH$_2$CH$_2$SCOCH$_3$ | 4-biphenylmethyl | —CH$_3$ | benzyl | 0 | 110–112 (HCO$_2$H) | 1:9.2 2:10.2 50% |
| 4 | H | H | phenyl | —CHOCOCH$_3$ \| CH$_3$ | 4-biphenylmethyl | —CH$_3$ | benzyl | 0 | 132–134 (HCO$_2$H) | 1:8.5 2:12.2 3:15.0 50% |
| 5 | H | H | CH$_3$ | —CH$_4$CH$_2$SCO-phenyl | 4-biphenylmethyl | CH$_3$ | benzyl | 0 | 125–127 (TFA) | 1:7.8 2:8.8 55% |

TABLE-continued (I)

$$\begin{array}{c} R_3 \\ | \\ R_1-N \\ | \\ R_2 \end{array} \begin{array}{c} O \\ \| \\ P-OR_4 \\ | \\ \end{array} \begin{array}{c} R_5 \\ | \\ \end{array} \begin{array}{c} R_7 \\ | \\ CONH \end{array} \begin{array}{c} R_7 \\ | \\ R_6 \end{array} _n COOR_8$$

| No. | R₁ | R₂ | R₃ | R₄ | R₅ | R₆ | R₈ | n | M.P. (°C.) | Tr (min) % aceto-nitrile |
|---|---|---|---|---|---|---|---|---|---|---|
| 6 | H | H | CH₃ | —CH₂CH₂SCO—C(CH₃)₂CH₃ | biphenyl-CH₂ | CH₃ | benzyl-CH₂ | 0 | 127–129 (TFA) | 1:8.3 2:9.3 55% |
| 7 | H | H | CH₃ | —CH₂CH₂SCOCH₂CH₃ | biphenyl-CH₂ | CH₃ | benzyl-CH₂ | 0 | 121–123 (TFA) | 1:9.1 2:11.2 55% |
| 8 | H | H | phenyl | —CH₂CH₂SCO-phenyl | biphenyl-CH₂ | CH₃ | benzyl-CH₂ | 0 | 127–129 (TFA) | 1:10.9 2:11.8 55% |
| 9 | H | H | phenyl | —CH₂CH₂SCO—C(CH₃)₂CH₃ | biphenyl-CH₂ | CH₃ | benzyl-CH₂ | 0 | 130–132 (TFA) | 1:11.4 2:12.6 55% |

TABLE-continued $$\begin{array}{c} R_3 \\ | \\ R_1-N-\underset{|}{\overset{|}{C}}-\underset{\|}{\overset{O}{P}}-OR_4 \\ R_2 \quad \overset{}{\underset{CONH}{}} \\ \quad\quad R_5 \\ \quad\quad | \\ \quad\quad \underset{R_7}{\overset{}{C}}H-\underset{R_6}{\overset{}{C}}H \\ \quad\quad\quad (\phantom{)}_n COOR_8 \end{array} \quad (I)$$

| No. | $R_1$ | $R_2$ | $R_3$ | $R_4$ | $R_5$ | $R_6$ | $R_8$ | n | M.P. (°C.) | Tr (min) % acetonitrile |
|---|---|---|---|---|---|---|---|---|---|---|
| 10 | H | H | 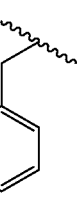 | —CH$_2$CH$_2$SCOCH$_2$CH$_3$ | 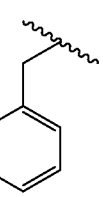 | CH$_3$ | 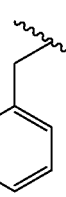 | 0 | 121–124 (TFA) | 1:12.1 2:14.2 55% |
| 11 | H | H | 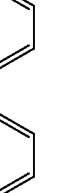 | —CH$_2$CH$_2$SCOCH$_3$ | 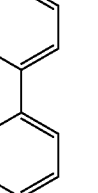 | CH$_2$OH | 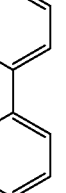 | 0 | 132–134 (TFA) | 1:8.5 2:8.9 55% |
| 12 | H | H | CH$_3$ | —CH$_2$CH$_2$SCOCH$_3$ | 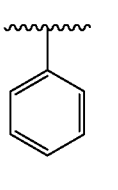 | CH$_2$OH |  | 0 | 128–130 (TFA) | 1:6.1 2:6.7 55% |

"TFA" means trifluoroacetate in the table

The compounds of the invention have been the object of enzymological tests permitting determining their inhibitive power as to NAP and APN.

Measure of the Inhibitory Power on Neutral Endopeptidase (NEP)

The inhibitory power is determined on purified neutral endopeptidase of rabbit kidney by following the protocol described in the literature (Llorens et al., *Neurochem.*, 39, 1081, 1982) After an incubation of 15 minutes at 25° C., an aliquot of proteins is incubated for 20 minutes at 37° C. in the presence of 20 nmoles of ($^3$H)D-Ala$^2$-Leu$^5$-enkephaline and of the compound to be tested in solution in a Tris HCl buffer (pH=7.4)

The reaction is stopped by the addition of 0.2N hydrochloric acid. The tritrated metabolite ($^3$H)-Tyr-D-Ala-Gly is separated from the D-Ala$^2$-Leu$^5$-enkephaline by chromatography on a Porapak column and the quantity of formed metabolite is measured with the help of a liquid scintillation counter.

The activity of the different compounds of the invention, expressed in inhibitory concentrations 50 (CI$_{50}$) varies from $10^{-6}$ to $10^{-9}$ M.

Inhibitory Power on Aminopentidase N (APN)

The inhibitory power is measured on purified aminopeptidase of pig liver (Boehringer, France). After a preincubation of 15 minutes at 25° C., an aliquot of proteins is incubated for 20 minutes at 25° C. in the presence of 20 nmoles of ($^3$H)-Leu-enkephaline and of the compound to be tested in solution in a tris HCl buffer (pH=7.4).

The reaction is stopped by the addition of 0.5 N hydrochloric acid. The formed metabolite ($^3$H)Tyr is separated by chromatography on a Porapak column and.the quantity of formed metabolite is measured with the help of a liquid scintillation counter.

The activity of the different compounds of the invention, expressed in inhibitory concentrations 50 (CI$_{50}$) varies from $10^{-6}$ to $10^{-9}$ M.

The compounds of the invention have also been the object of pharmacological tests permitting measuring their analgesic activity.

Hot Plate Test with Mice

The test is carried out 15 minutes after administration by intracerebroventricular route of increasing doses of the compounds of the invention, in mice.

Two parameters are measured: the latency time of jumping and the latency of licking.

The results are expressed in DE$_{50}$, which is to say the doses giving half the maximum response. The analgesic activity of the different compounds of the invention falls between 1 and 100 μg/kg. The activity of the compounds of the invention is the most active between 1 and 20 μg/kg.

Another protocol consists in studying the effect of the compounds after administration by the intravenous route at times of 30, 60, 90, 120, 150 and 180 min, at the dosage of 50 mg/kg. The measured parameters are the time of latency of jumping and the time of latency of licking.

The analgesic activity of the compounds is expressed in percentage of times of latency relative to the time of maximum latency of 240 seconds.

The activity of the most active compounds is situated between 30 and 70%.

A third protocol consists in studying the antinociceptive effect of the compounds after administration by the intraperitoneal route at times of 30, 60, 90, 120, 150 and 180 min after administration. The compounds are administered in a single dose of 50 mg/kg.

The analgesic activity is expressed in percentage of the time of latency relative to the time of maximum latency (240 seconds).

The activity of the most active compounds is located between 30 and 70% of analgesia.

The compounds of the invention have a mixed NAP/APN in vitro activity and an in vivo analgesic activity; these results show that the compounds of the invention can be used as analgesics.

The compounds according to the invention can also be used for the preparation of medications for the treatment of depressive conditions of all nature, sleep disorders, anxiety disorders, cognitive and vigilance disorders, and peripheral disorders (diarrhea, coughing, hypertension, inflammation . . . ).

The invention also has for its object pharmaceutical compositions comprising as active principle at least one of the compounds of formula (I) or their addition salts in admixture with an acceptable excipient.

The compounds of the invention can be present, in association with excipients, in the form of compositions formulated for administration by enteral or parenteral route, for example in the form of tablets, pills, granules, powders, dragees, capsules, solutions, suspensions, injectable solutions, elixers or syrups.

The salt solutions of the compounds of the invention are particularly useful for administration by intramuscular or subcutaneous injection.

The compounds of the invention are administered at a daily dose comprised between 0.01 and 100 mg/kg, preferably between 0.1 and 10 mg/kg.

Annex 1

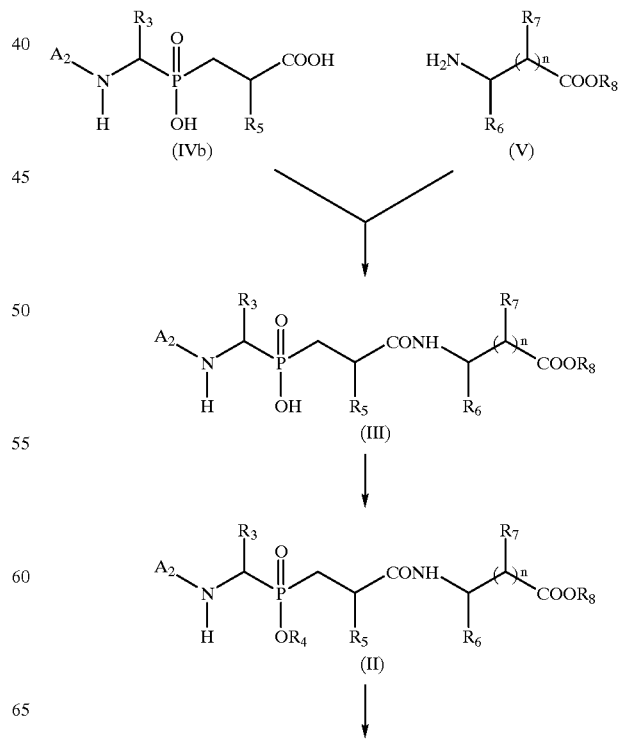

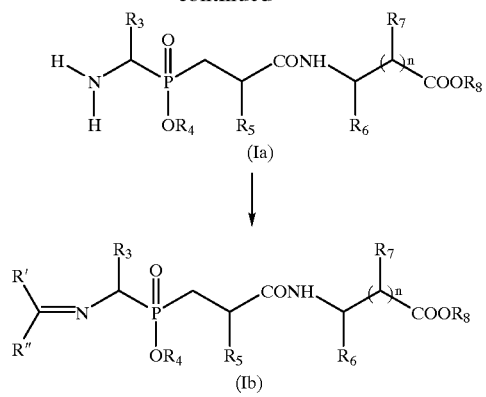
(Ia)
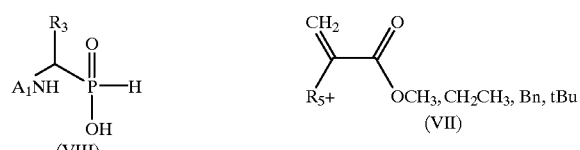
(Ib)
Annex 2
Diagram 1
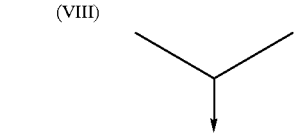
(VIII)
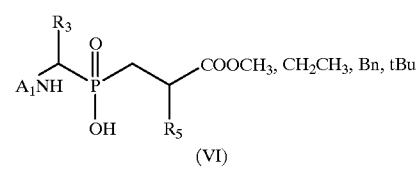
(VII)
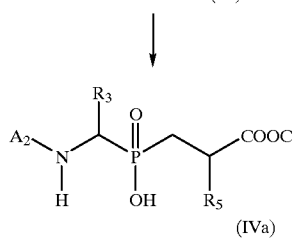
(VI)
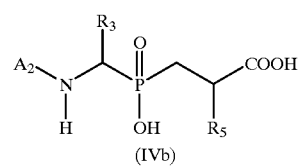
(IVa)
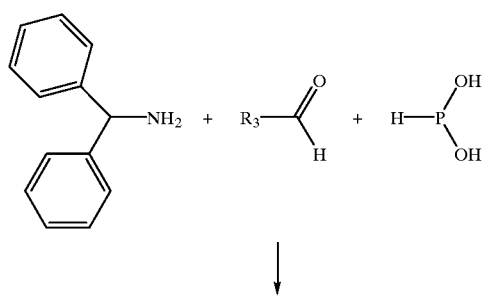
(IVb)
Diagram 2
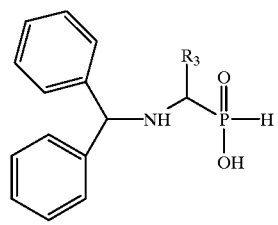
(IX)
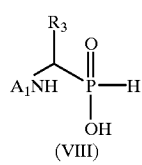
(VIII)
Annex 3
Diagram 3
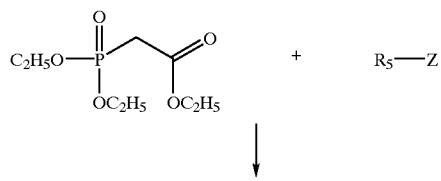
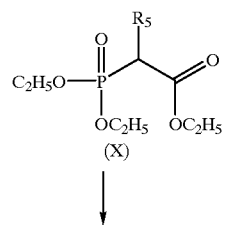
(X)
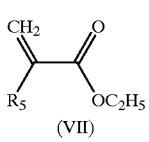
(VII)
Diagram 4
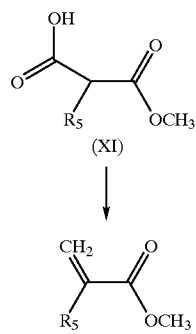
(XI)
(VII)

What is claimed is:

1. A compound of the formula (I)

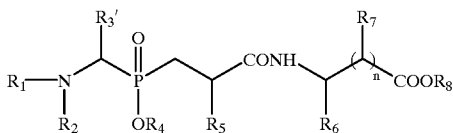

in which $R_1$ and $R_2$ each represent a hydrogen atom or $R_1$ and $R_2$, taken together, form an unsaturated group of the formula $R'(R'')C=$, in which:
  R' represents a phenyl group in position 2 monosubstituted with a hydroxy group or a disubstituted phenyl group, in position 2, with a hydroxy group and, in position 4 or 5, either by a halogen atom or by a nitro group, or by a hydroxy group, or by an alcoxy group —$OR_9$,
  R" represents a phenyl group, a phenyl group substituted with 1 to 5 halogen atoms or an aromatic heterocyclic group, $R_3$ represents one of the following:
  a hydrogen atom,
  an alkyl group or an alkenyl group of 1 to 6 carbon atoms, these two latter groups can be substituted by:
    a hydroxy group or an alcoxy group —$OR_9$,
    a phenyl group or a benzyl group,
    a sulfanyl group, an alkylsulfanyl group —$SR_9$ or an alkylsulfanyl group oxidized at the sulfur atom —$S(O)R_9$,
    an amino group, an —$NHR_9$ group or —$NR_9R_{10}$ group, if desired oxidized at the nitrogen atom or,
    a guanidino group $H_2N$—$C(=NH)$—$NH$—,
  a cycloalkyl or cycloalkylmethyl group,
  a phenyl group, a benzyl group, which can be substituted on the phenyl group with 1 or 2 of the following substituents:
    a halogen atom,
    a hydroxy group, an alcoxy group —$OR_9$,
    an alkylsulfanyl group —$SR_9$ or an alkylsulfanyl group oxidized at the sulfur atom,
    an amino group or a —$NHR_9$ or —$NR_9R_{10}$ group if desired oxidized at the nitrogen atom,
    a nitro group,
    a phenyl group,
    an alkyl group of 1 to 4 carbon atoms,
  a methyl group substituted by an aromatic or saturated heterocyclic group, the heteroatoms being possibly oxidized in the form of N-oxide or S-oxide, $R_4$ represents one of the following:
  a —$CH(X)$—$O$—$C(O)$—$Y$ group, in which X and Y represent, independently of each other, an $R_9$ group or a phenyl group,
  a —$CH_2CH_2$—$S$—$C(O)$—$W$ group, in which W represents an $R_9$ group or a phenyl group, $R_5$ represents one of the following:
  a hydrogen atom,
  an alkyl group or an alkenyl group of 1 to 6 carbon atoms, these two latter groups being possibly substituted with:
    a hydroxy group or an alcoxy group —$OR_9$,
    a phenyl group or a benzyl group,
    a sulfanyl group, an alkylsulfanyl group —$SR_9$ or an alkylsulfanyl group oxidized at the sulfur atom —$S(O)R_9$,
    an amino group, an —$NHR_9$ or —$NR_9R_{10}$ group, possibly oxidized at the nitrogen atom or,
    a guanidino group $H_2N$—$C(=NH)$—$NH$—,
  a cycloalkyl or cycloalkylmethyl group,
  a phenyl group, a benzyl group, which can be substituted at the phenyl group by 1 or 2 of the following substituents:
    a halogen atom,
    a hydroxy group, an alcoxy group —$OR_9$,
    an alkylsulfanyl group —$SR_9$ or an alkylsulfanyl group oxidized at the sulfur atom,
    an amino group or an —$NHR_9$ or —$NR_9R_{10}$ group which can be oxidized at the nitrogen atom,
    a nitro group,
    a phenyl group,
    an alkyl group of 1 to 4 carbon atoms,
  a methyl group substituted with a heterocyclic group, the hetero atoms can be oxidized in the form of N-oxide or S-oxide, $R_6$ and $R_7$ represent independently of each other
  a hydrogen atom,
  an alkyl or alkenyl group of 1 to 6 carbon atoms, which can be substituted with:
    a hydroxy or an alcoxy group —$OR_9$,
    a sulfanyl group, an alkylsulfanyl group —$SR_9$ or an alkylsulfanyl group oxidized at the sulfur atom —$S(O)R_9$,
    an amino group or an alkylamino group —$NHR_9$,
    a guanidino group $H_2N$—$C(=NH)$—$NH$— or,
    a carboxy group or an alkyloxycarbonyl group —$COOR_9$,
  a phenyl group, a benzyl group, which can be substituted on the phenyl group by 1 or 2 of the following substituents:
    a halogen atom,
    a phenyl group,
    a hydroxy group or an alcoxy group —$OR_9$,
    an alkylsulfanyl group —$SR_9$ or an alkylsulfanyl group oxidized at the sulfur atom —$S(O)R_9$, $R_6$ and $R_7$ together represent a saturated or unsaturated cyclic compound of 5 or 6 members, comprising 1 or 2 heteroatoms selected from oxygen, sulfur and nitrogen, $R_8$ represents one of the following:
  an alkyl or alkenyl group of 1 to 6 carbon atoms,
  a phenyl group, a benzyl group, $R_9$ and $R_{10}$ each represent an alkyl group of 1 to 6 carbon atoms, and n is equal to 0 or 1, in the form of isomers including in the form of enantiomers and diastereoisomers and of mixtures of these different forms, including racemic mixtures as well as their pharmacologically acceptable acid addition salts.

2. Compound according to claim 1, wherein
  $R_1$ and $R_2$ represent hydrogen atoms,
  n is equal to 0,
  $R_3$ represents one of the following:
    a hydrogen atom,
    an alkyl group of 1 to 6 carbon atoms, which can be substituted with a hydroxy group, an alcoxy group —$OR_9$, a sulfanyl group or an alkylsulfanyl group —$SR_9$,
    a phenyl group, a benzyl group which can be substituted on the phenyl group with a halogen atom, an alkyl group of 1 to 4 carbon atoms, a hydroxy group, an alcoxy group —$OR_9$ or an alkylsulfanile group —$SR_9$, $R_4$ represents one of the following:
- a —CH(X)—O—C(O)—Y group, wherein X and Y represent, independently of each other, an $R_9$ group or a phenyl group,
- a —CH$_2$CH$_2$—S—C(O)—W group, wherein W represents an $R_9$ group or a phenyl group, $R_5$ represents one of the following:
- a phenyl group, a benzyl group, which can be substituted on the phenyl group with a halogen atom, an alkyl group of 1 to 4 carbon atoms, a hydroxy group, an alcoxy group —OR$_9$ or an alkylsulfanyl group —SR$_9$,
- a biphenylmethyl group, $R_6$ represents an alkyl group of 1 to 6 carbon atoms, which can be substituted with a hydroxy group, an alcoxy group —OR$_9$, a sulfanyl group or an alkylsulfanyl group —SR$_9$, $R_8$ represents one of the following:
- an alkyl group of 1 to 6 carbon atoms,
- a phenyl group, a benzyl group.

3. Process for the preparation of compounds of the formula (Ia)

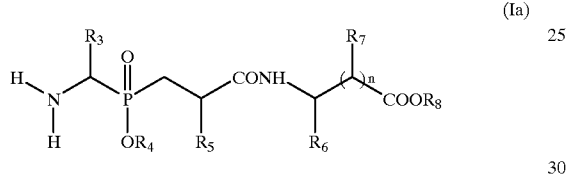

(Ia)

in which $R_3$, $R_4$, $R_5$, $R_6$, $R_7$, $R_8$ and n are as defined in claim 1, which consists:
in contacting a compound of the formula (IVb)

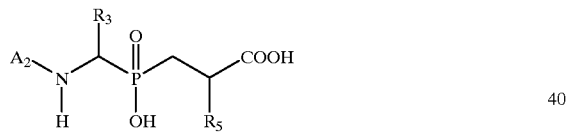

(IVb)

with a compound of the formula (V)

(V)

in which
$R_3$, $R_5$, $R_6$, $R_7$, $R_8$ and n are as defined in claim 1, and A2 represents a tert-butoxycarbonyle group or a fluorenylmethoxycarbonyl group, in the presence of benzotriazol-1-yloxy-tris(dimethylamino) phosphonium hexafluorophosphate (BOP) or with 1-ethyl-3-(3-dimethylaminopropyl)carbodiimide methiodide (EDC) to obtain a compound of the formula (III)

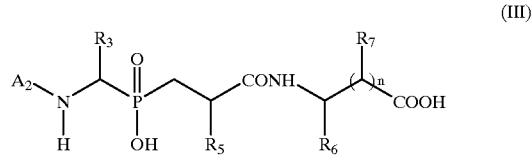

(III)

and contacting the resulting compound with an alcohol of formula $R_4$OH, in which $R_4$ is as defined in claim 1, in the presence of N,N'-dicyclohexylcarbodiimide and 4-dimethylaminopyridine to obtain a compound of the formula (II)

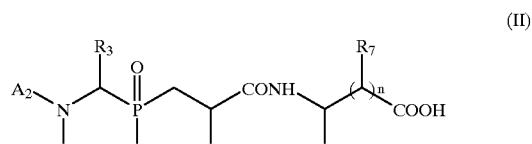

(II)

then removing the protective group of the amine function to obtain a compound of formula (Ia) or else
transforming a compound of formula (III) as obtained as before with a cesium salt, and contacting this salt with a halogenated derivative $R_4Z$, in which Z represents a halogen atom selected from the group consisting of bromine, chlorine and iodine and $R_4$ is as defined above, to obtain the compound of formula (II), then removing the protective function so of the amine group to obtain a compound of formula (Ia).

4. Process for the preparation of compounds of formula (Ib)

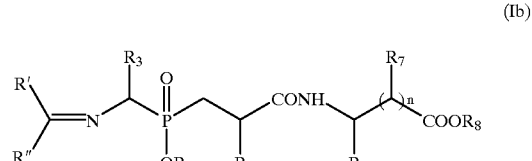

(Ib)

in which R', R", $R_3$, $R_4$, $R_5$, $R_6$, $R_7$, $R_8$ and n are as defined in claim 1, which consists in condensing a ketone R'(R")C=O on a compound of formula (Ia), as prepared in claim 3, said ketone being obtained by a Fries rearrangement of a corresponding ester R"CO$_2$R'.

5. Pharmaceutical composition wherein it contains a compound according to claim 1, in association with any suitable excipient.

* * * * *